(12) United States Patent
Palmerton et al.

(10) Patent No.: US 12,364,506 B2
(45) Date of Patent: Jul. 22, 2025

(54) FILTRATION DEVICE AND SYSTEM

(71) Applicant: Buffalo Filter LLC, Lancaster, NY (US)

(72) Inventors: Christopher A. Palmerton, Clarence, NY (US); Samantha Bonano, Williamsville, NY (US); Anthony Lizauckas, Williamsville, NY (US); Kyrylo Shvetsov, Tonawanda, NY (US); Daniel R. Palmerton, Elma, NY (US); Gregory Pepe, Lancaster, NY (US); Joseph Lynch, Williamsville, NY (US)

(73) Assignee: Buffalo Filter LLC

( * ) Notice: Subject to any disclaimer, the term of this patent is extended or adjusted under 35 U.S.C. 154(b) by 269 days.

(21) Appl. No.: 17/578,535

(22) Filed: Jan. 19, 2022

(65) Prior Publication Data

US 2022/0133349 A1 May 5, 2022

Related U.S. Application Data

(63) Continuation of application No. 14/759,731, filed as application No. PCT/US2013/074610 on Dec. 12, 2013, now Pat. No. 11,259,839.

(Continued)

(51) Int. Cl.
*A61B 17/34* (2006.01)
*A61B 90/30* (2016.01)
*B01D 53/04* (2006.01)

(52) U.S. Cl.
CPC .......... *A61B 17/3421* (2013.01); *A61B 90/30* (2016.02); *B01D 53/04* (2013.01);
(Continued)

(58) Field of Classification Search
CPC .......... A61B 17/3421; A61B 2217/005; A61B 2217/007; A61B 2218/008
See application file for complete search history.

(56) References Cited

U.S. PATENT DOCUMENTS

| | | |
|---|---|---|
| 3,596,441 A | 8/1971 | Lundahl |
| 3,736,728 A | 6/1973 | Kleissler |

(Continued)

FOREIGN PATENT DOCUMENTS

| | | |
|---|---|---|
| EP | 2305157 A1 | 4/2011 |
| KR | 10-0909672 B1 | 7/2009 |

(Continued)

OTHER PUBLICATIONS

Ball, Controlling Smoke Evacuation and Odor During Laser Surgery, Today's OR Nurse, vol. 8, No. 12, Dec. 1986.

(Continued)

*Primary Examiner* — Jessica Arble
(74) *Attorney, Agent, or Firm* — Timothy W. Menasco, Esq.; Harter Secrest & Emery LLP

(57) ABSTRACT

A fluid filtration device having an outer cylindrical surface with a first diameter having a longitudinal axis, and an inner cylindrical surface with an inner diameter substantially centered about the longitudinal axis, and a plurality of longitudinal holes substantially parallel to the longitudinal axis arranged between the outer cylindrical surface and the inner cylindrical surface.

7 Claims, 4 Drawing Sheets

Related U.S. Application Data

(60) Provisional application No. 61/736,078, filed on Dec. 12, 2012.

(52) U.S. Cl.
CPC ... *A61B 17/3417* (2013.01); *A61B 2017/3437* (2013.01); *A61B 2017/3445* (2013.01); *A61B 2217/005* (2013.01); *A61B 2217/007* (2013.01); *A61B 2218/008* (2013.01); *B01D 2257/80* (2013.01)

(56) References Cited

U.S. PATENT DOCUMENTS

| | | |
|---|---|---|
| 3,858,572 A | 1/1975 | Binard et al. |
| 3,903,727 A | 9/1975 | Sweet |
| 4,048,992 A | 9/1977 | Lindemann et al. |
| 4,106,213 A | 8/1978 | Witte |
| 4,220,633 A | 9/1980 | Pirsh |
| 4,270,725 A | 6/1981 | Scott et al. |
| 4,324,574 A | 4/1982 | Fagan |
| 4,382,440 A | 5/1983 | Kapp et al. |
| 4,451,258 A | 5/1984 | Jensen |
| 4,477,270 A | 10/1984 | Tauch |
| 4,487,606 A | 12/1984 | Leviton et al. |
| 4,538,594 A | 9/1985 | Boebel et al. |
| 4,561,868 A | 12/1985 | von Reis et al. |
| 4,571,244 A | 2/1986 | Knighton |
| 4,735,603 A | 4/1988 | Goodson et al. |
| 4,787,894 A | 11/1988 | Turnbull |
| 4,813,931 A | 3/1989 | Hauze |
| 4,874,513 A | 10/1989 | Chakraborty et al. |
| 4,906,261 A | 3/1990 | Mohajer |
| 4,930,997 A | 6/1990 | Bennett |
| 4,936,318 A | 6/1990 | Schoolman |
| 4,957,492 A | 9/1990 | McVay |
| 5,002,534 A | 3/1991 | Rosenblatt |
| 5,047,010 A | 9/1991 | Ams et al. |
| 5,069,792 A | 12/1991 | Prince et al. |
| 5,098,375 A | 3/1992 | Baier |
| 5,127,411 A | 7/1992 | Schoolman et al. |
| 5,244,619 A | 9/1993 | Burnham |
| 5,246,419 A | 9/1993 | Absten |
| 5,249,579 A | 10/1993 | Hobbs et al. |
| 5,279,549 A | 1/1994 | Ranford |
| 5,336,169 A | 8/1994 | Divilio et al. |
| 5,360,396 A | 11/1994 | Chan |
| 5,364,377 A | 11/1994 | O'Neil |
| 5,417,655 A | 5/1995 | Divilio et al. |
| 5,451,222 A | 9/1995 | De Maagd et al. |
| 5,578,000 A | 11/1996 | Greff et al. |
| 5,634,905 A | 6/1997 | Rudolph, Jr. |
| 5,688,256 A | 11/1997 | Surratt et al. |
| 5,709,675 A | 1/1998 | Williams |
| 5,722,962 A | 3/1998 | Garcia |
| 5,824,138 A | 10/1998 | Taylor, III |
| 5,897,525 A | 4/1999 | Dey et al. |
| 6,110,259 A | 8/2000 | Schultz et al. |
| 6,203,590 B1 | 3/2001 | Byrd et al. |
| 6,517,551 B1 | 2/2003 | Driskill |
| 6,544,210 B1 | 4/2003 | Trudel et al. |
| 6,576,033 B1 | 6/2003 | Booth |
| 6,585,791 B1 | 7/2003 | Garito et al. |
| 6,589,316 B1 | 7/2003 | Schultz et al. |
| 6,592,543 B1 | 7/2003 | Wortrich et al. |
| 6,746,504 B2 | 6/2004 | Booth |
| 6,881,236 B2 | 4/2005 | Schultz et al. |
| 7,204,810 B2 | 4/2007 | Hynes et al. |
| 7,258,712 B2 | 8/2007 | Schultz et al. |
| 7,402,197 B2 | 7/2008 | Larsen et al. |
| 7,789,946 B2 | 9/2010 | Schultz et al. |
| 7,819,954 B2 | 10/2010 | Larsen et al. |
| 7,819,957 B2 | 10/2010 | Roberts et al. |
| 7,857,806 B2 | 12/2010 | Karpowicz et al. |
| 7,959,698 B2 | 6/2011 | Schultz et al. |
| 8,114,181 B2 | 2/2012 | Gogolin |
| 8,608,816 B2 | 12/2013 | Palmerton et al. |
| 9,415,160 B2 | 8/2016 | Bonano et al. |
| 9,867,914 B2 | 1/2018 | Bonano et al. |
| 11,259,839 B2 * | 3/2022 | Palmerton .............. A61B 90/30 |
| 2002/0128603 A1 | 9/2002 | Booth et al. |
| 2003/0183082 A1 | 10/2003 | Schultz et al. |
| 2004/0128962 A1 | 7/2004 | Jeanfreau |
| 2005/0000196 A1 | 1/2005 | Schultz |
| 2005/0015043 A1 | 1/2005 | Stubbs et al. |
| 2005/0022810 A1 | 2/2005 | Moore et al. |
| 2005/0203342 A1 | 9/2005 | Kucklick et al. |
| 2006/0149225 A1 | 7/2006 | McClurken |
| 2007/0137484 A1 | 6/2007 | Roberts |
| 2007/0249990 A1 | 10/2007 | Cosmescu |
| 2008/0234674 A1 | 9/2008 | McClurken et al. |
| 2009/0043314 A1 | 2/2009 | Sevensson et al. |
| 2009/0054825 A1 | 2/2009 | Melsheimer et al. |
| 2009/0101562 A1 | 4/2009 | Newton |
| 2009/0221963 A1 | 9/2009 | Lloyd et al. |
| 2010/0094200 A1 | 4/2010 | Dean et al. |
| 2011/0028891 A1 | 2/2011 | Okoniewski |
| 2012/0078038 A1 * | 3/2012 | Sahney .............. A61B 17/3421 600/104 |
| 2012/0245511 A1 | 9/2012 | Stearns et al. |
| 2012/0316512 A1 | 12/2012 | Ott et al. |
| 2013/0174525 A1 | 7/2013 | Palmerton et al. |
| 2014/0165842 A1 | 6/2014 | Bonano et al. |
| 2014/0236129 A1 | 8/2014 | Radl et al. |
| 2014/0243599 A1 | 8/2014 | Farin et al. |
| 2014/0249574 A1 | 9/2014 | Piskun et al. |

FOREIGN PATENT DOCUMENTS

| | | |
|---|---|---|
| WO | 2008109014 A2 | 9/2008 |
| WO | 2009111259 A1 | 9/2009 |

OTHER PUBLICATIONS

Descoteaux, Preliminary study of electrocautery smoke particles produced in vitro and during laparoscopic procedures, Surgical Endoscopy, vol. 10, 1996, p. 152-158.

Pall Medical Brochure, Gas Filtration Products for OEM Health Care Devices, 2003, Pall Corporation.

* cited by examiner

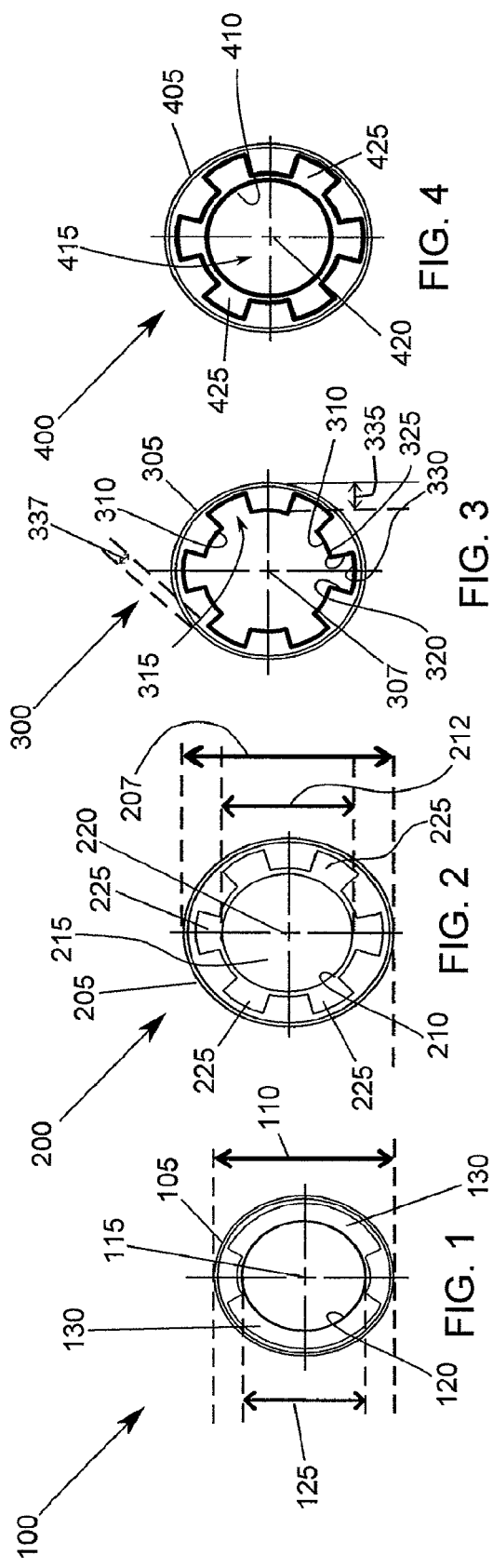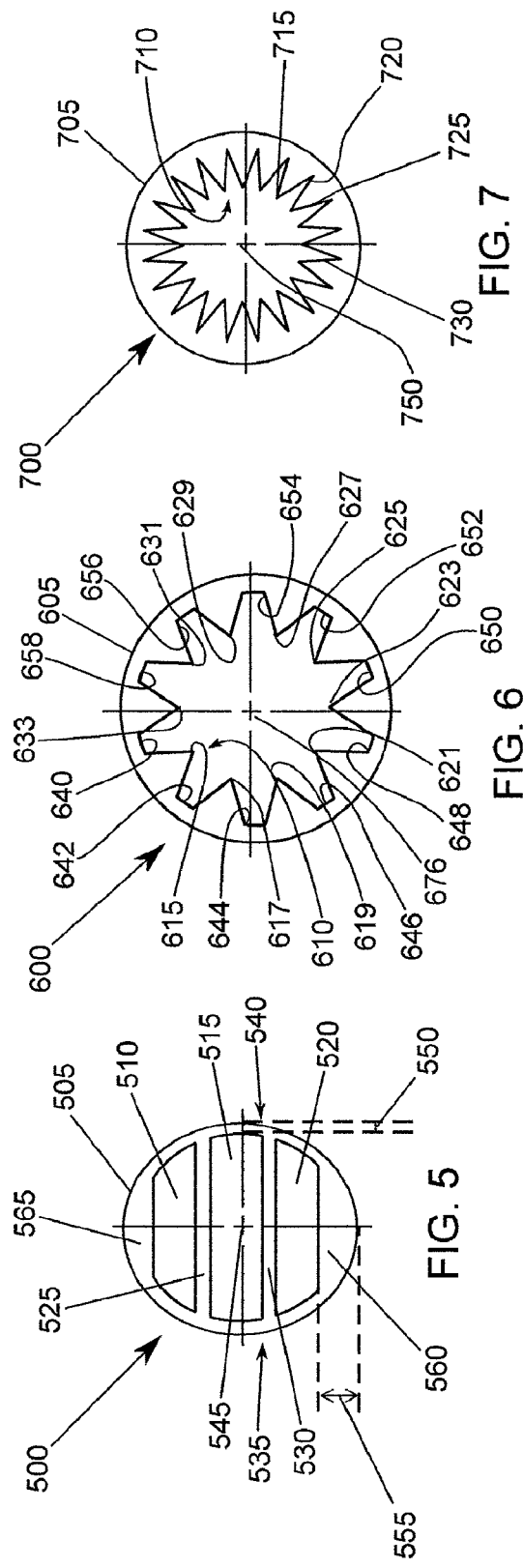

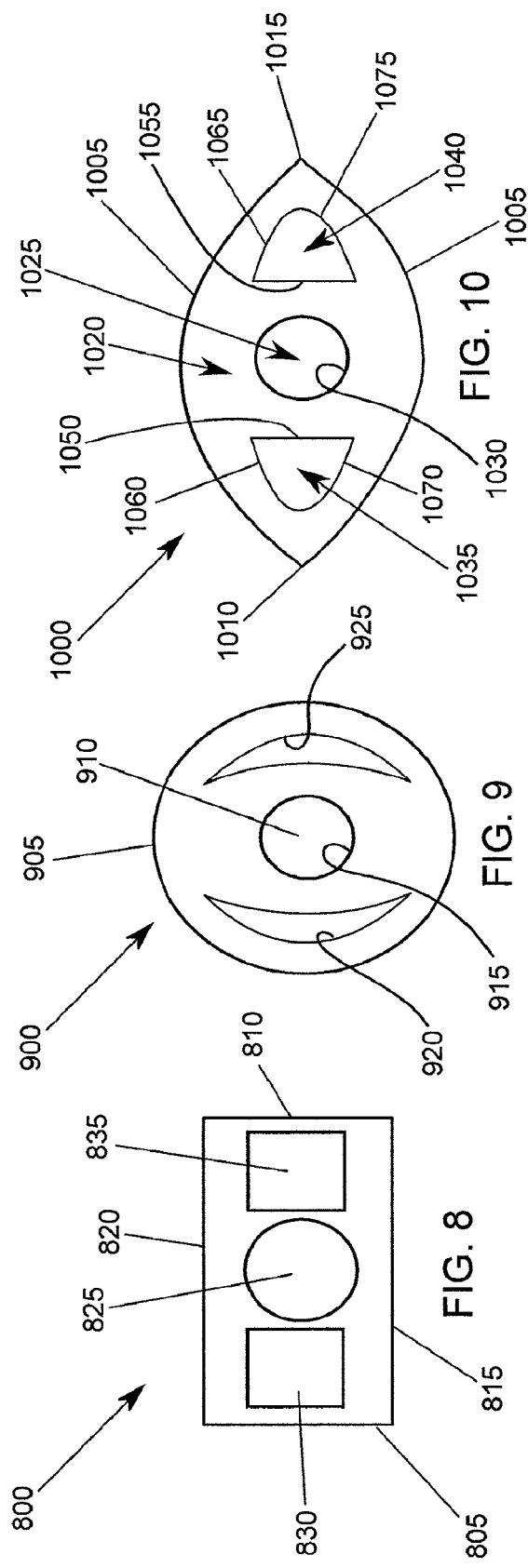

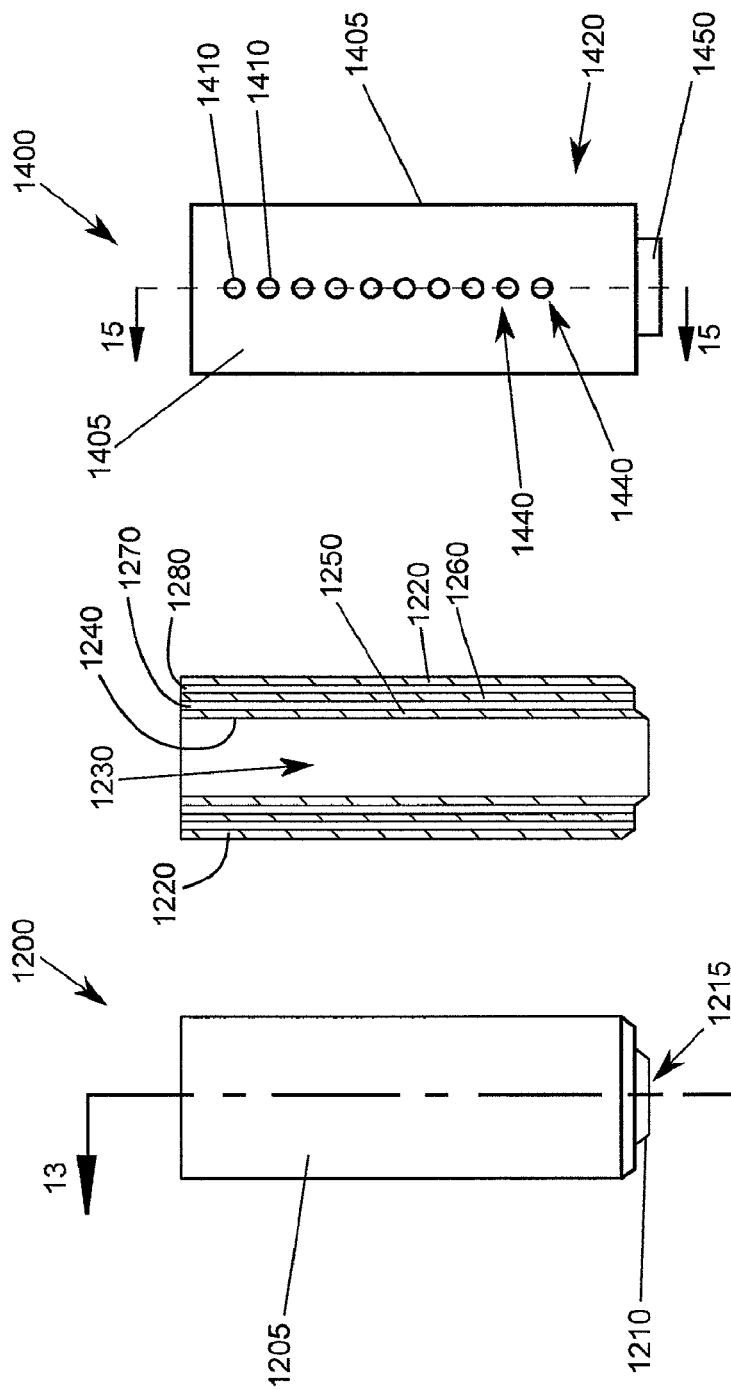

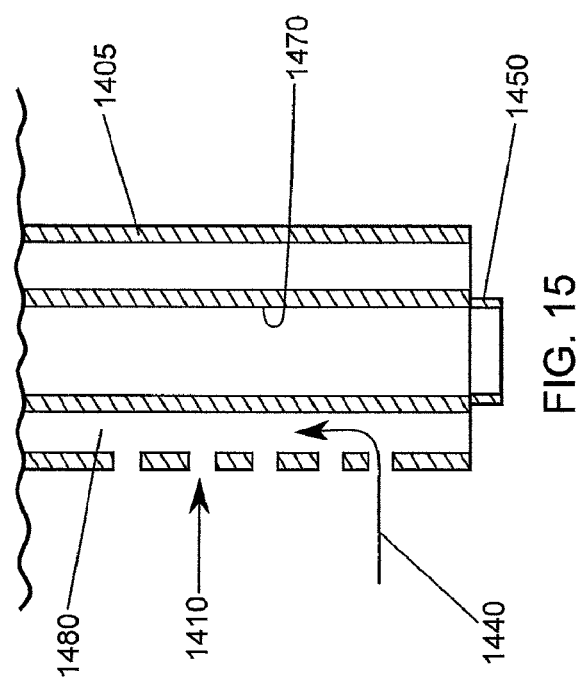

FILTRATION DEVICE AND SYSTEM

CROSS REFERENCE TO RELATED APPLICATIONS

This application claims priority from U.S. Provisional Patent Application No. 61/736,078, entitled "Filtration Device and System" filed on Dec. 12, 2012, which is hereby incorporated by reference.

TECHNICAL FIELD

The present invention relates generally to fluid filtration in a medical environment, and more specifically to methods and devices for fluid filtration with a trocar.

SUMMARY OF THE INVENTION

With parenthetical reference to the corresponding parts, portions or surfaces of the disclosed embodiment, merely for the purposes of illustration and not by way of limitation, provided is a fluid filtration device (100, 200, 300, 400, 500, 600, 700, 800, 900, 1000, 1100) having an outer cylindrical surface with a first diameter having a longitudinal axis, and an inner cylindrical surface with an inner diameter substantially centered about the longitudinal axis, and a plurality of longitudinal holes substantially parallel to said longitudinal axis arranged between said outer cylindrical surface and said inner cylindrical surface. The longitudinal holes may be notches, and may be generally rectangular or generally triangular notches. The total number of longitudinal holes may be two, six, ten, twelve, or other similar number. The longitudinal holes may have a cross-sectional area equal to approximately one-half of the cross-sectional area between the outer cylindrical surface and the inner cylindrical surface. The outer cylindrical surface may have a number of holes along the surface perpendicular to the longitudinal axis. The longitudinal holes may define a plurality of independent passages and/or channels passing through said device. Each channel may be optimized for a different function. One of the functions may be suction, one function may be irrigation, another function may be insufflation. The device may be configured to be inserted through a body wall into a surgical site. The device may be a cannula, and the cannula may be configured to spring open when pressed through an abdominal wall. The device may have a fiber optic guide for illumination. The device may contain a light or LED for illumination. The device may include a camera. The device may have a pressure sensor, temperature sensor, and/or humidity sensor. The device may be telescopic and/or collapsible. One or more of the passageways/channels may have a fluid trap, filter, and or moisture absorber. The device may have a multiple instrument seal. The device may include a swivel, and the swivel may be a two-dimensional swivel. The device may use a skin substitute as part or a whole portion of the device. A portion of the cylindrical outer surface may be flexible. The device may contain a cooler or a heater.

The outer cylindrical surface and the inner cylindrical surface may he non-parallel such that the first cylindrical surface and the second cylindrical surface have a cross section at one level forming a generally figure-eight shaped surface and a cross section at a second level where the first cylindrical surface and the second cylindrical surface are generally concentric. The cannula may be ionized to attached particles in a fluid, and the particles may be dust particles. The device may include a safety pressure relief valve.

In another aspect the first cylindrical surface and the second cylindrical surface do not circumscribe each other.

In another aspect, provided is a fluid filtration device having an outer rectangular prism surface having a longitudinal axis, and an inner cylindrical surface with an inner diameter substantially centered about the longitudinal axis, and a plurality of longitudinal holes substantially parallel to said longitudinal axis arranged between said outer rectangular prism surface and said inner cylindrical surface.

In another aspect, provided is a fluid filtration device having an outer surface with an oval-shaped cross section having a longitudinal axis, and an inner cylindrical surface with an inner diameter substantially centered about the longitudinal axis, and a plurality of longitudinal holes substantially parallel to said longitudinal axis arranged between said outer oval-shaped surface and said inner cylindrical surface.

One of the channels may be optimized for use with a smoke evacuation system. The device may have an adapter similar to a luer-lock adapter, or alternatively may have an adapter which is a straight hose connection, a push-to-lock type connector, and/or may have a cross section larger than a typical luer-lock connector to allow increased flow.

The device may also have a mechanical anchor to hold the device to an interior body wall. The device may have a ball and socket joint on a top portion to allow tool movement. The device may contain special nanotechnology based filtration media. The device may include a multi-lumen tubing. The multi-lumen tubing may be bi-lumen or tri-lumen tubing.

BRIEF DESCRIPTION OF THE DRAWINGS

FIG. 1 is a cross sectional view of a first embodiment filtration device.

FIG. 2 is a cross sectional view of a second embodiment filtration device.

FIG. 3 is a cross sectional view of a third embodiment filtration device.

FIG. 4 is a cross sectional view of a fourth embodiment filtration device.

FIG. 5 is a cross sectional view of a fifth embodiment filtration device.

FIG. 6 is a cross sectional view of a sixth embodiment filtration device.

FIG. 7 is a cross sectional view of a seventh embodiment filtration device.

FIG. 8 is a cross sectional view of an eighth embodiment filtration device.

FIG. 9 is a cross sectional view of a ninth embodiment filtration device.

FIG. 10 is a cross sectional view of a tenth embodiment filtration device.

FIG. 11 is a cross sectional view of an eleventh embodiment filtration device.

FIG. 12 is a side view of a first type of side for a filtration device.

FIG. 13 is a cross sectional view taken along lines 13-13 of FIG. 12.

FIG. 14 is a second type of side for a filtration device.

FIG. 15 is a cross sectional view taken along lines 15-15 of FIG. 14.

DESCRIPTION OF EMBODIMENTS

At the outset, it should be clearly understood that like reference numerals are intended to identify the same structural elements, portions, or surfaces consistently throughout the several drawing figures, as such elements, portions, or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal," "vertical," "left," "right," "up," and "down," as well as adjectival and adverbial derivatives thereof (e.g., "horizontally," "rightwardly," "upwardly," etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, FIG. 1 discloses a first embodiment 100 of a device and/or system for filtering a fluid. Fluid filter system 100 comprises an outer cylindrical surface 105 with a first diameter 110 having a longitudinal axis 115, and an inner cylindrical surface 120 with an inner diameter 125 substantially centered about the longitudinal axis 115, and a plurality of longitudinal holes 130 substantially parallel to said longitudinal axis arranged between said outer cylindrical surface 105 and said inner cylindrical surface 120. As shown in FIG. 1, the holes 130 are in the form of rectangular-shaped cross section cutouts that span the length of the device.

Turning to FIG. 2, a second embodiment 200 of a device and/or system for filtering a fluid is shown. Device 200 has outer cylindrical surface 205 having a diameter 207 and inner cylindrical surface 210 having a diameter 212. The inner cylindrical surface 210 borders a central opening 215. The outer and inner cylindrical surfaces 205, 210 are disposed parallel to a central, longitudinal axis 220. A plurality of longitudinal holes 225 are disposed in the device 200 between in the inner and outer cylindrical surfaces 210, 205. In the example shown there are six longitudinal holes 225 that provide channels as will be described in greater detail below.

Turning to FIG. 3, a third embodiment 300 of a device and/or system for filtering a fluid is shown. Device 300 has an outer cylindrical surface 305. Device 300 may be symmetrical about a central longitudinal axis 307. An inner cylindrical surface 310 has notches cut out to form channels 315. The notch forms a pair of side walls 320 and 325 that lead to a bottom wall 330 that is disposed in spaced apart relation to the outer cylindrical surface 305. As a result, the device 300 has a first thickness 335 between the inner and outer cylindrical surfaces 305, 310 and has a second thickness 337 between the bottom wall 330 and the outer cylindrical surface 305. The result is a series of channels disposed about the central longitudinal axis 307 and extending for the length of the device 300.

In FIG. 4, a fourth embodiment 400 of a device and/or system for filtering a fluid is shown. Device 400 has outer cylindrical surface 405 and inner cylindrical surface 410. The inner cylindrical surface 410 borders a central opening 415. The outer and inner cylindrical surfaces 405, 410 are disposed parallel to a central, longitudinal axis 420. A plurality of longitudinal holes 425 are disposed in the device 400 between in the inner and outer cylindrical surfaces 410, 405. In the example shown there are six longitudinal holes 425 that provide channels as will be described in greater detail below.

Turning to FIG. 5, a fifth embodiment device 500 has an outer cylindrical surface 505. The interior of the device is divided into three channels 510, 515, and 520. The channels 510, 515, and 520 are separated by dividing walls 525 and 530 extending from a first side 535 to a second side 540 of the device 500. The device 500 is symmetrical about a central longitudinal axis 545. The sides 535 and 540 have a first thickness 550 which is smaller than a second thickness 555 located at opposite ends 560, 565 of the device 500.

In FIG. 6, a sixth embodiment device 600 is shown. Device 600 has an outer cylindrical surface 605. The inside surface 610 of the device 600 is formed from a plurality of peaks 615, 617, 619, 621, 623, 625, 627, 629, 631, 633 disposed opposite from flat surfaces 640, 642, 644, 646, 648, 650, 652, 654, 656, and 658. Device 600 may be symmetrical about a central longitudinal axis 676.

Turning to FIG. 7, a seventh embodiment device 700 is shown. The device 700 has an outer cylindrical surface 705. The inside surface 710 is defined by a plurality of alternating peaks 715 and valleys 720. The peaks 715 and valleys 720 are formed by the convergence of angled surfaces 725 and 730 that form triangular shaped notches in the inner surface 710 of the device 700. The device 700 is also symmetrical about a central longitudinal axis 750.

In FIG. 8, an eighth embodiment device 800 has a rectangular shape in cross-section. A first side surface 805 is disposed opposite from a second side surface 810. A third side surface 815 is disposed opposite from a fourth side surface 820. The device 800 is provided with a central round opening 825 that leads to a longitudinal channel A pair of square or rectangular openings 830 and 835 are disposed on opposite sides of the central opening 825.

In FIG. 9, a ninth embodiment device 900 has an outer cylindrical surface 905. A central longitudinal channel 910 is bordered by an inner cylindrical surface 915. On opposite sides of the channel 910, a pair of crescent shaped longitudinal channels 920 and 925 are disposed in the device 900.

Turning to FIG. 10, a tenth embodiment device 1000 has an oval-shaped outer surface 1005. The oval-shaped outer surface 1005 extends from a first endpoint 1010 to a second endpoint 1015 disposed opposite from the first endpoint 1010. In a mid-portion 1020 of the device 1000, a central longitudinal channel 1025 is bordered by an inner cylindrical surface 1030 that extends along the length of the device 1000. On opposite sides of the central channel 1025, a pair of channels 1035 and 1040 are formed in the device 1000. In cross-section, the channels 1035 and 1040 have a "D" shape formed by a straight wall 1050, 1055; an upper curved portion 1060, 1065; and a lower curved portion 1070, 1075. The "D" shaped channels formed on either side of the central channel 1025 are mirror images of each other.

As shown in FIGS. 1-10, the longitudinal holes are notches with a generally rectangular or triangular cross section. In the embodiments shown, the number of longitudinal holes is two, six, ten, twelve, and alternatively may be another similar number. The longitudinal holes shown may have a cross-sectional area equal to approximately one-half of the cross sectional area between the outer cylindrical surface and the inner cylindrical surface.

The longitudinal holes define a plurality of independent passages or channels passing through the device 100, 200, 300, 400, 500, 600, 700, 800, 900, 1000 and 1100. Each channel is optimized for a different function. One of the channels may be used for suction, another for insufflation, and in embodiments with more than two longitudinal holes, another channel may be configured for irrigation. The embodiments are configured to be inserted through a body wall into a surgical site. The device longitudinal portion is generally a cannula, and the cannula may be configured to spring open when pressed through an abdominal wall. The device may have a fiber optic guide for illumination. The device 100, 200, 300, 400, 500, 600, 700, 800, 900, 1000 and 1100 also may have a light in the form of an LED for illumination. The first embodiment 100 also may include a camera, a pressure sensor, a temperature sensor, and/or a humidity sensor. In other embodiments, the device may be telescopic and/or collapsible.

In other embodiments, one or more of the passageways/channels may have a fluid trap, filter, and/or moisture absorber. The device may have a multiple instrument seal. Other embodiments may contain a swivel, and the swivel may be a two dimensional swivel. The device may use a skin substitute as part of or as a whole portion of the device. A portion of the cylindrical outer surface may be flexible. Additional embodiments may contain a cooler or a heater.

In additional embodiments, the outer cylindrical surface and the inner cylindrical surface may be non-parallel such that the first cylindrical surface and the second cylindrical surface have a cross section at one level forming a generally figure-eight shaped surface and a cross-section at a second level where the first cylindrical surface and the second cylindrical surface are generally concentric. The cannula may be ionized to attached particles in a fluid, and the particles may be dust particles. The device may include a safety pressure relief valve.

In FIG. 11, in device 1100 the outer cylindrical surface and the inner cylindrical surface may be nonparallel such that the first cylindrical surface 1105 and the second cylindrical surface 1110 have a cross section at one level forming a generally figure-eight shaped surface.

FIG. 12 and FIG. 13 provide side view and side sectional views respectively of a first form of the outer cylinder of the embodiments. In FIG. 12, a fluid filtration device 1200 has an outer cylindrical surface 1205. At the bottom of the figure a reduced diameter section 1210 terminates at a bottom opening 1215. The device 1200 may be configured to be inserted through a body wall into a surgical site. The device 1200 may be a cannula, and the cannula may be configured to spring open when pressed through an abdominal wall. Turning to FIG. 13, the device 1200 has an outer cylindrical wall 1220. An inner passageway 1230 is bordered by an inner cylindrical surface 1240 on an inner cylindrical wall 1250. A space between the inner wall 1250 and the outer wall 1220 is divided by a third wall 1260. The third wall 1260 divides the space into two sections 1270 and 1280.

FIG. 14 is a side view of a second form of the outer cylinder of the embodiments which contains a plurality of openings 1410 on the outer cylindrical surface 1405. The openings 1410 on the outer cylindrical surface 1405 communicate with one of the channels formed by one of the longitudinal holes shown in FIG. 1. The device 1400 has an outer cylindrical surface 1405 that may be provided with a plurality of openings 1410 disposed along the length of the device 1400 toward the bottom portion 1420. The device 1400 may have an inner cylindrical surface 1470. A longitudinal channel 1480 is formed between the inner and outer cylindrical surfaces 1470, 1405. The openings 1410 provide a fluid passageway along arrows 1440 when the end 1450 of the device 1400 is covered by tissue or the like that may come into contact with the end 1450 of the device 1400 and block the flow of fluid into the device 1400.

Therefore, while the presently-preferred form of the filtration device has been shown and described, and several modifications discussed, persons skilled in this art will readily appreciate that various additional changes may be made without departing from the scope of the invention.

What is claimed is:

1. A fluid filtration system for use during minimally invasive surgical procedures involving a surgical site accessed through a body wall, the surgical site having higher than ambient pressure, the system comprising:
    a first elongate tubular member having a first end, a second end disposed opposite from the first end, an inner surface, an outer surface and a longitudinal axis, the first elongate tubular member having a plurality of openings disposed near the second end, the openings extending through the first elongate tubular member, the first elongate tubular member configured to be inserted through the body wall into the surgical site;
    a plurality of channels disposed inside the first elongate tubular member, at least one of the plurality of channels being disposed in fluid communication with at least one of the openings extending through the first elongate tubular member, the plurality of channels being oriented substantially parallel to the longitudinal axis, wherein the plurality of channels comprises a first and a second channel each having a "D" shaped cross section and a third channel having a circular cross section, wherein the first and second channels are mirror images of each other; and,
    wherein at least one of the plurality of channels is configured to convey smoke from the surgical site during the surgical procedure.

2. The system of claim 1, wherein the outer surface of the first elongate tubular member is cylindrical.

3. The system of claim 1, wherein the inner surface of the first elongate tubular member is cylindrical.

4. The device of claim 1, wherein the first elongate tubular member is oval in cross section.

5. The device of claim 1, wherein at least one of the plurality of channels is configured for suction from the surgical site during the surgical procedure.

6. The device of claim 1, wherein at least one of the plurality of channels is configured for insufflation by conveying a gas to the surgical site during the surgical procedure.

7. The device of claim 1, wherein at least one of the plurality of channels is configured for irrigation by conveying a fluid to the surgical site during the surgical procedure.

* * * * *